US 6,730,654 B2

(12) United States Patent
Godfroid et al.

(10) Patent No.: US 6,730,654 B2
(45) Date of Patent: May 4, 2004

(54) ANTIMICROBIAL COMPOSITIONS FOR HARD SURFACES CONTAINING BIGUANIDE COMPOUNDS

(75) Inventors: Robert Allen Godfroid, West Chester, OH (US); Christopher James Binski, Cincinnati, OH (US); Joseph Paul Morelli, Kirkland, WA (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/401,196

(22) Filed: Mar. 27, 2003

(65) Prior Publication Data

US 2003/0186830 A1 Oct. 2, 2003

Related U.S. Application Data

(63) Continuation of application No. 09/671,080, filed on Sep. 27, 2000, now Pat. No. 6,559,116, which is a continuation-in-part of application No. 09/655,221, filed on Sep. 5, 2000
(60) Provisional application No. 60/156,289, filed on Sep. 27, 1999.

(51) Int. Cl.⁷ .............................. C11D 3/48; C11D 3/37
(52) U.S. Cl. ................. 510/499; 510/238; 510/384; 510/356; 510/362; 510/365; 510/421; 510/504; 510/237; 510/235; 510/386; 510/387; 510/388
(58) Field of Search ................................. 510/499, 238, 510/384, 356, 362, 365, 421, 504, 237, 235, 386, 387, 388

(56) References Cited

U.S. PATENT DOCUMENTS

| | | | |
|---|---|---|---|
| 3,627,687 A | 12/1971 | Teumac et al. | |
| 4,561,991 A | 12/1985 | Herbots et al. | |
| 4,787,998 A | 11/1988 | Rennie et al. | |
| 4,880,558 A | * 11/1989 | Jost et al. | 252/174.23 |
| 5,008,030 A | * 4/1991 | Cook et al. | 252/106 |
| 5,348,678 A | 9/1994 | Hodam, Jr. et al. | |
| 5,935,920 A | 8/1999 | Geke et al. | |
| 5,962,388 A | * 10/1999 | Sherry et al. | 510/238 |
| 6,045,817 A | 4/2000 | Ananthapadmanabhan et al. | |
| 6,340,663 B1 | 1/2002 | Deleo et al. | |

FOREIGN PATENT DOCUMENTS

| | | |
|---|---|---|
| EP | 0206513 | 12/1986 |
| EP | 342997 | * 11/1989 |
| EP | 03442997 | 11/1989 |
| EP | 0197649 | 5/1990 |
| EP | 0342997 | 8/1994 |
| EP | 0414304 | 11/1994 |
| EP | 0911022 | 4/1999 |
| EP | 0971021 | 1/2000 |
| EP | 0987321 | 3/2000 |
| GB | 1349567 | 4/1974 |
| GB | 2144763 | 3/1985 |
| JP | 6311492 | 11/1996 |
| WO | WO 93/15177 | 8/1993 |
| WO | WO 97/35067 | 9/1997 |

* cited by examiner

*Primary Examiner*—Charles Boyer
(74) *Attorney, Agent, or Firm*—Thibault Fayette; Kim William Zerby; Steven W. Miller

(57) ABSTRACT

Antimicrobial, hard surface cleaning compositions that effectively clean and reduce microorganisms on a surface without resulting in unacceptable filming and/or streaking residue on the surface, generally comprise (a) cationic antimicrobial active; (b) nitrogen-containing polymer; and (c) surfactant. Preferred antimicrobial, hard surface cleaning compositions for use in no-rinse cleaning methods comprise (a) from about 0.001% to about 0.5%, by weight of the composition, of surfactant; (b) cationic antimicrobial active; and (c) nitrogen-containing polymer. Methods of cleaning and reducing microorganisms on hard surfaces comprises contacting the surfaces with such compositions and preferably allowing the compositions to dry on the surface without rinsing the composition from the surface using water or other rinsing solution.

20 Claims, No Drawings

ANTIMICROBIAL COMPOSITIONS FOR HARD SURFACES CONTAINING BIGUANIDE COMPOUNDS

CROSS REFERENCE TO RELATED APPLICATION

This application is a continuation of U.S. application Ser. No. 09/671,080 filed Sep. 27, 2000 U.S. Pat. No. 6,559,116 which claims the benefit of U.S. Provisional Application Serial No. 60/156,289 filed Sep. 27, 1999 by R. A. Godfroid et al. (P&G Case 7800P) and which is a continuation-in-part of U.S. Ser. No. 09/655,221 allowed filed Sep. 5, 2000 by R. A. Godfroid et al. (P&G Case 7800).

TECHNICAL FIELD

The present invention relates to antimicrobial detergent compositions for reducing microorganisms on hard surfaces and for cleaning hard surfaces, as well as methods of reducing microorganisms on hard surfaces and cleaning hard surfaces. The present antimicrobial compositions and methods minimize the amount of streaks left on the treated surfaces, even in situations where the compositions are not rinsed from the treated surface.

BACKGROUND OF THE INVENTION

Hard surface cleaning compositions having antimicrobial effectiveness are known in the art. Such compositions are able to both clean soils from surfaces and reduce microorganisms present on surfaces. However, many of these compositions are not suitable for many hard surfaces, such as ceramic tile, vinyl, linoleum, finished wood floors, laminates, and the like, because the compositions tend to leave significant filming and/or streaking of the surface, resulting in an appearance that is unacceptable to consumers. A number of attempts have been made to address the filming and/or streaking problems associated with these types of compositions.

For example, EP 342,997 B2 granted to Rennie et al. disclose a general-purpose cleaning composition comprising from 0.01 to 90% by weight of a nonionic surfactant, 0.005 to 50% by weight of a cationic surfactant which has a sanitising action, and 0.003 to 20% by weight of a non-anionic polymer which has an adsorptive affinity to hard surfaces. Rennie et al. teach that its compositions usually contain from 0.1 to 30% by weight of nonionic surfactant, and that its compositions should contain at least 1% of nonionic surfactant to obtain both reduced streaking and improved cleaning effects.

Others have developed compositions utilizing cationic polymer and antimicrobial biguanide compounds to provide sanitization of other types of surfaces, such as human skin. For example, U.S. Pat. No. 6,045,817, issued Apr. 4, 2000 to Ananthapadmanabhan et al. discloses an antibacterial cleaning composition containing from about 0.05% to about 1% of a cationic polymer having a charge density of 0.0025 or higher, from about 0.2 to about 5% of a zwitterionic surfactant, from about 0.2% to about 5% of at least one biguanide compound, optionally nonionic surfactant and a polymeric biocide compound, and has a pH of 7.5 or greater. The composition of the '817 patent is used for handwashing purposes and is said to exhibit improved mildness, while providing antimicrobial effectiveness.

However, antimicrobial hard surface cleaning compositions still lead to filming and/or streaking problems on hard surfaces that are unacceptable to consumers, especially when the compositions are left to dry on the surface without rinsing. As a result, consumers typically rinse such compositions from the treated surfaces with water in order to reduce the residue left by such compositions.

It has thus been desired to develop an antimicrobial, hard surface cleaning composition that is able to effectively clean soils from surfaces, reduce microorganisms on the surface (i.e. disinfect the surface), while leaving the surface essentially free of filming and/or streaking, even when such compositions are left to dry on the surface without rinsing.

SUMMARY OF THE INVENTION

The present invention relates to antimicrobial, hard surface cleaning compositions that effectively clean and reduce microorganisms on a surface without resulting in unacceptable filming and/or streaking residue on the surface. The present compositions generally comprise (a) cationic antimicrobial active; (b) nitrogen-containing polymer; and (c) surfactant. Preferred antimicrobial, hard surface cleaning compositions of the present invention for use in no-rinse cleaning methods typically comprise (a) from about 0.001% to about 0.5%, by weight of the composition, of surfactant; (b) cationic antimicrobial active; and (c) nitrogen-containing polymer.

The present invention further relates to methods of cleaning and reducing microorganisms on hard surfaces comprising contacting the surfaces with such compositions and preferably allowing the compositions to dry on the surface without rinsing the composition from the surface using water or other rinsing solution.

The present invention further encompasses kits for cleaning and reducing microorganisms on surfaces comprising a container having therein such compositions and a disposable cleaning pad having a $t_{1200}$ absorbent capacity of at least about 1 gram of water per gram of cleaning pad.

DETAILED DESCRIPTION OF THE INVENTION

I. COMPOSITIONS

The present invention encompasses antimicrobial compositions for cleaning and/or disinfecting hard surfaces, especially household surfaces such as ceramic tile, vinyl, linoleum, finished wood floors, laminates, and the like. The antimicrobial compositions of the present invention generally comprise (a) cationic antimicrobial active; (b) nitrogen-containing polymer; and (c) surfactant. The present compositions can further comprise optional ingredients such as aqueous carrier, buffer, perfume, suds suppressor, and the like.

It has been found that incorporating nitrogen-containing polymers, especially certain types of modified polyamine polymers, in hard surface cleaning compositions containing cationic antimicrobial actives serves to substantially eliminate much of the filming and/or streaking residue left on surfaces by such compositions that do not contain nitrogen-containing polymers, especially when such compositions are used in "no-rinse" cleaning methods. As used herein, the term "no-rinse" refers to cleaning methods wherein the cleaning composition is allowed to dry on the surface being cleaned without rinsing the composition from the surface with water (or other rinsing solutions).

It has further been found that incorporating such nitrogen-containing polymers in hard surface cleaning compositions also significantly helps the wetting and spreading properties of the composition, to allow for better surface coverage and better cleaning and disinfecting performance. Indeed, the preferred compositions herein provide contact angles, as measured according to the Contact Angle Measurement Test Method as described in Section IV infra, of less than about 30°, preferably less than about 20°, and more preferably less than about 15°.

The antimicrobial, hard surface cleaning compositions herein relate to both traditional all-purpose cleaning compositions used in traditional cleaning methods, and also to low-surfactant compositions preferably used in no-rinse cleaning methods. Traditional all-purpose cleaning compositions tend to comprise a wide range of surfactant levels, as well as other components, and can be used neat or can be diluted to form dilute cleaning compositions. Such compositions are typically applied to the surface to be cleaned and then rinsed from the surface with water (or other rinsing solutions).

The preferred antimicrobial, hard surface cleaning compositions herein comprise relatively low levels of surfactant (i.e. levels of surfactant less than about 0.5%, by weight of the composition) and are preferably used in no-rinse cleaning methods. Such compositions can be applied to the surface to be cleaned and then allowed to dry on the surface without rinsing the composition from the surface with water (or other rinsing solutions). Even in such no-rinse cleaning methods, these compositions do not leave unsightly filming and/or streaking on the treated surface. As a result, such compositions are highly acceptable and desirable to consumers, since they are easy to use (e.g. no need for rinsing) and provide an acceptable end cleaning result.

A. CATIONIC ANTIMICROBIAL ACTIVES

The compositions herein comprise cationic antimicrobial actives such that the compositions are capable of reducing or killing microorganisms on surfaces to be treated with the compositions. A variety of cationic antimicrobial actives can be used in the present compositions. However, as mentioned hereinbefore, compositions comprising cationic antimicrobial actives tend to leave unsightly filming and/or streaking on the treated surfaces. As a result, the compositions herein should further comprise a nitrogen-containing polymer, especially a modified polyamine polymer as described infra, to mitigate this effect.

Cationic antimicrobial actives useful herein are preferably selected from the group consisting of $C_6$–$C_{18}$ alkyltrimethylammonium chlorides, $C_6$–$C_{18}$ dialkyldimethylammonium chlorides, $C_6$–$C_{18}$ alkylbenzyldimethylammonium chloride, chlorhexidine diacetate, chlorhexidine dihydrochloride, chlorhexidine digluconate, benzethonium chloride, and mixtures thereof. Particularly preferred cationic antimicrobial actives herein are chlorhexidine, or salts thereof, and dialkyldimethylammonium chlorides.

The preferred compositions herein comprise two or more different cationic antimicrobial actives to provide enhanced antimicrobial efficacy. Preferably, the compositions comprise at least one quaternary cationic antimicrobial active and at least one biguanide antimicrobial active. Such actives are preferably in a ratio of quaternary cationic antimicrobial active to biguanide antimicrobial active of from about 10:1 to about 1:10, and more preferably from about 5:1 to about 1:5, by weight.

In a preferred embodiment, the antimicrobial, hard surface cleaning composition of the present invention comprises a chlorhexidine salt, preferably chlordexidine diacetate, and a dialkyldimethylammonium chloride, preferably didecyldimethylammonium chloride (Bardac® 2250).

In general, the antimicrobial, hard surface cleaning compositions of the present invention comprise cationic antimicrobial active at a level of from about 0.005% to about 10%, preferably from about 0.005% to about 5%, and more preferably from about 0.005% to about 1%, by weight of the composition.

In preferred low-surfactant compositions for use in no-rinse cleaning methods, such compositions typically comprise cationic antimicrobial active at a level of from about 0.005% to about 1%, preferably from about 0.005% to about 0.5%, and more preferably from about 0.005% to about 0.2%, by weight of the composition.

1. Quaternary Compounds

A wide range of quaternary compounds can also be used as antimicrobial actives, in conjunction with the preferred surfactants. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Witco/Sherex), and Hyamine® (available from Lonza); (2) di($C_6$–$C_{14}$)alkyl di short chain ($C_{1-4}$ alkyl and/or hydroxyalkl) quaternary such as Bardac® products of Lonza, (3) N-(3-chloroallyl) hexaminium chlorides such as Dowicide® and Dowicil® available from Dow; (4) benzethonium chloride such as Hyamine® from Rohm & Haas; (5) methylbenzethonium chloride represented by Hyamine® 10 X supplied by Rohm & Haas, (6) cetylpyridinium chloride such as Cepacol chloride available from of Merrell Labs. Examples of the preferred dialkyl quaternary compounds are di($C_8$–$C_{12}$)dialkyl dimethyl ammonium chloride, such as didecyldimethylammonium chloride (Bardac 22), and dioctyldimethylammonium chloride (Bardac 2050). The quaternary compounds useful as cationic antimicrobial actives herein are preferably selected from the group consisting of dialkyldimethylammonium chlorides, alkyldimethylbenzylammonium chlorides, dialkylmethylbenzylammonium chlorides, and mixtures thereof. Other preferred cationic antimicrobial actives useful herein include diisobutylphenoxyethoxyethyl dimethylbenzylammonium chloride (commercially available under the trade name Hyamine® 1622 from Rohm & Haas) and (methyl)diisobutylphenoxyethoxyethyl dimethylbenzylammonium chloride (i.e. methylbenzethonium chloride). Typical concentrations for biocidal effectiveness of these quaternary compounds, especially in the preferred low-surfactant compositions herein, range from about 0.001% to about 0.8%, preferably from about 0.005% to about 0.3%, more preferably from about 0.005% to about 0.08%, and even more preferably from about 0.005% to about 0.06%, by weight of the usage composition.

The surfactants, as described infra, when added to the present compositions, tend to provide improved antimicrobial action.

2. Biguanides

Other useful cationic antimicrobial actives herein include biguanide compounds, either. alone or in combination with other cationic antimicrobial actives. Especially useful biguanide compounds include 1,1'-hexamethylene bis(5-(p-chlorophenyl)biguanide), commonly known as chlorhexidine, and its salts, e.g., with hydrochloric, acetic and gluconic acids. The digluconate salt is highly water-soluble, about 70% in water, and the diacetate salt has a solubility of about 1.8% in water. When chlorhexidine is used as a cationic antimicrobial active in the present invention it is typically present at a level of from about 0.001% to about 0.4%, preferably from about 0.002% to about 0.1%, and more preferably from about 0.005% to about 0.06%, by weight of the usage composition. In some cases, a level of from about 0.09% to about 1% may be needed for virucidal activity.

Other useful biguanide compounds include Cosmocil® CQ®, Vantocil®IB, including poly(hexamethylene biguanide) hydrochloride. Other useful cationic antimicrobial actives include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like.

Examples of suitable bis biguanide compounds are chlorhexidine; 1,6-bis-(2-ethylhexylbiguanidohexane) dihydrochloride; 1,6-di-($N_1,N_1$'-phenyldiguanido-$N_5,N_5$')-hexane tetrahydrochloride; 1,6-di-($N_1,N_1$'-phenyl-$N_1,N_1$'-methyldiguanido-$N_5,N_5$')-hexane dihydrochloride; 1,6-di ($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di[$N_1,N_1$'-.beta.-(p-methoxyphenyl)diguanido-$N_5,N_5$']-hexane dihydrochloride; 1,6-di($N_1,N_1$'-.alpha.-methyl-.beta.-phenyldiguanido-$N_5,N_5$')-hexane dihydrochloride; 1,6-di($N_1,N_1$'-p-nitrophenyldiguanido-$N_5,N_5$')hexane dihydrochloride; .omega.:.omega.'-di-($N_1,N_1$'-phenyldiguanido-$N_5,N_5$')-di-n-propylether dihydrochloride; .omega:omega'-di($N_1,N_1$'-p-chlorophenyldiguanido-$N_5,N_5$')-di-n-propylether tetrahydrochloride; 1,6-di($N_1,N_1$'-2,4-dichlorophenyldiguanido-$N_5,N_5$')hexane tetrahydrochloride; 1,6-di($N_1,N_1$'-p-methylphenyldiguanido-$N_5,N_5$')hexane dihydrochloride; 1,6-di($N_1,N_1$'-2,4,5-trichlorophenyldiguanido-$N_5,N_5$') hexane tetrahydrochloride; 1,6-di[$N_1,N_1$'.alpha.-(p-chlorophenyl)ethyldiguanido-$N_5,N_5$']hexane dihydrochloride; .omega.:.omega.'di($N_1,N_1$'-p-chlorophenyldiguanido-$N_5,N_5$')m-xylene dihydrochloride; 1,12-di($N_1,N_1$'-p-chlorophenyldiguanido-$N_5,N_5$')dodecane dihydrochloride; 1,10-di($N_1,N_1$'-phenyldiguanido-$N_5,N_5$')-decane tetrahydrochloride; 1,12-di($N_1,N_1$'-phenyldiguanido-$N_5,N_5$') dodecane tetrahydrochloride; 1,6-di($N_1,N_1$'-o-chlorophenyldiguanido-$N_5,N_5$')hexane dihydrochloride; 1,6-di($N_1,N_1$'-p-chlorophenyldiguanido-$N_5,N_5$')-hexane tetrahydrochloride; ethylene bis(1-tolyl biguanide); ethylene bis(p-tolyl biguanide); ethylene bis(3,5-dimethylphenyl biguanide); ethylene bis(p-tert-amylphenyl biguanide); ethylene bis(nonylphenyl biguanide); ethylene bis(phenyl biguanide); ethylene bis(N-butylphenyl biguanide); ethylene bis(2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenylbiguanide); trimethylene bis(o-tolyl biguanide); N-butyl trimethylene bis (phenyl biguanide); and the corresponding pharmaceutically acceptable salts of all of the above such as the acetates; gluconates; hydrochlorides; hydrobromides; citrates; bisulfites; fluorides; polymaleates; N-coconutalkylsarcosinates; phosphites; hypophosphites; perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; and perfluoropropionates, and mixtures thereof. Preferred antimicrobials from this group are 1,6-di-($N_1,N_1$'-phenyldiguanido-$N_5,N_5$')-hexane tetrahydrochloride; 1,6-di($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di($N_1,N_1$'-2,4-dichlorophenyldiguanido-$N_5,N_5$')hexane tetrahydrochloride; 1,6-di[$N_1,N_1$'-.alpha.-(p-chlorophenyl) ethyldiguanido-$N_5,N_5$']hexane dihydrochloride; .omega.:.omega.'di($N_1,N_1$'-p-chlorophenyldiguanido-$N_5,N_5$')m-xylene dihydrochloride; 1,12-di($N_1,N_1$'-p-chlorophenyldiguanido-$N_5,N_5$')dodecane dihydrochloride; 1,6-di($N_1,N_1$'-o-chlorophenyldiguanido-$N_5,N_5$')hexane dihydrochloride; 1,6-di($N_1,N_1$'-p-chlorophenyldiguanido-$N_5,N_5$')-hexane tetrahydrochloride; and mixtures thereof; more preferably, 1,6-di($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di($N_1,N_1$'-2,4-dichlorophenyldiguanido-$N_5,N_5$')hexane tetrahydrochloride; 1,6-di[$N_1,N_1$'-.alpha.-(p-chlorophenyl) ethyldiguanido-$N_5,N_5$']hexane dihydrochloride; .omega.:.omega.'di($N_1,N_1$'-p-chlorophenyldiguanido-$N_5$, $N_5$')m-xylene dihydrochloride; 1,12-di($N_1,N_1$'-p-chlorophenyldiguanido-$N_5,N_5$')dodecane dihydrochloride; 1,6-di($N_1,N_1$'-o-chlorophenyldiguanido-$N_5,N_5$')hexane dihydrochloride; 1,6-di($N_1,N_1$'-p-chlorophenyldiguanido-$N_5,N_5$')-hexane tetrahydrochloride; and mixtures thereof. As stated hereinbefore, the bis biguanide of choice is chlorhexidine and its salts, e.g., digluconate, dihydrochloride, diacetate, and mixtures thereof.

B. NITROGEN-CONTAINING POLYMERS

It has been surprisingly found that certain polymers, e.g. nitrogen-containing polymers, tend to mitigate the unwanted filming and/or streaking associated with compositions for cleaning hard surfaces that contain cationic antimicrobial actives, especially quaternary and/or biguanide antimicrobial actives.

Nitrogen-containing polymers useful herein include polymers that contain amines (primary, secondary, and tertiary), amine-N-oxide, amides, urethanes, and/or quaternary ammonium groups. It is important that the polymers herein contain nitrogen-containing groups that tend to strongly interact with the surface being treated in order to displace the cationic antimicrobial actives from the surface.

Preferably, the polymers herein contain basic nitrogen groups. Basic nitrogen groups include primary, secondary, and tertiary amines capable of acting as proton acceptors. Thus the preferred polymers herein can be nonionic or cationic, depending upon the pH of the solution. Polymers useful herein can include other functional groups, in addition to nitrogen groups. The preferred polymers herein are also essentially free of, or free of, quaternary ammonium groups.

Preferably, the polymers herein are branched polymers, especially highly branched polymers including comb, graft, starburst, and dendritic structures. Preferably, the polymers herein are not linear polymers.

The nitrogen-containing polymers herein can be an unmodified or modified polyamine, especially an unmodified or modified polyalkyleneimine. Preferably, the nitrogen containing polymers herein are modified polyamines. Poly ($C_2$–$C_{12}$ alkyleneimines) include simple polyethyleneimines and polypropyleneimines as well as more complex polymers containing these polyamines. Polyethyleneimines are common commercial materials produced by polymerization of aziridine or reaction of (di)amines with alkylenedichlorides. Polypropyleneimines are also included herein.

Although modified polyamines are preferred, linear or branched polyalkyleneimines, especially polyethyleneimines or polypropyleneimines, can be suitable in the present compositions to mitigate filming and/or streaking resulting from such compositions containing cationic antimicrobial actives. Branched polyalkyleneimines are preferred to linear polyalkyleneimines. Suitable polyalkyleneimines typically have a molecular weight of from about 1,000 to about 30,000 Daltons, and preferably from about 4,000 to about 25,000 Daltons. Such polyalkyleneimines are free of any ethoxylated and/or propoxylated groups, as it has been found that ethoxylation or propoxylation of polyalkyleneimines reduces or eliminates their ability to mitigate the filming and/or streaking problems caused by compositions containing cationic antimicrobial actives.

In general, the antimicrobial, hard surface cleaning compositions of the present invention comprise nitrogen-containing polymer at a level of from about 0.005% to about 10%, preferably from about 0.005% to about 5%, and more preferably from about 0.005% to about 1%, by weight of the composition.

In preferred low-surfactant compositions for use in no-rinse cleaning methods, such compositions typically comprise nitrogen-containing polymer at a level of from about 0.005% to about 1%, preferably from about 0.005% to about 0.3%, and more preferably from about 0.005% to about 0.1%, by weight of the composition.

Modified Polyamine Compounds

The nitrogen-containing polymers of the present invention can be comprised of one or more modified polyamines according to the present invention. The modified polyamines of the present invention can be formulated as an admixture wherein a proportional amount of two or more compounds are combined to make up the nitrogen-containing polymers herein.

Alternatively, the formulator can adjust the reaction conditions which form the modified polyamines of the present invention in order to create an admixture of suitable ingredients such as, inter alia, an admixture of polyamine fragments and/or partially crosslinked modified polyamines. Whether a formulated admixture or a product by process is used, or a mixture of both, the compounds which comprise the preferred nitrogen-containing polymers of the present invention generally are selected from the group consisting of:

(a) polyethyleneimine;
(b) polypropyleneimine; and
(c) modified polyamines having the formulae:

$(PA)_w(T)_x$;  (i)

$(PA)_w(L)_z$;  (ii)

or $[(PA)_w(T)_x]_y[L]_z$;  (iii)

wherein PA is a grafted or non-grafted, modified or unmodified polyamine backbone unit, T is an amide-forming polycarboxylic acid crosslinking unit, and L is a non-amide forming crosslinking unit. For compounds of type (i) and (iii) the relative amounts of PA units and T units which are present are such that the molar ratio of PA units to T units is from 0.8:1 to 1.5:1. For compounds of type (ii) the relative amounts of PA units and L units which are present are such that the $(PA)_w(L)_z$ comprises from about 0.05, preferably from about 0.3 to 2 parts by weight of said L units. Therefore, 1 part of a grafted or non-grafted, modified or unmodified polyamine backbone unit may be combined with from about 0.05, preferably from about 0.3 parts by weight of an L unit to about 2 parts by weight of an L unit to form a suitable modified polyamine compound. Likewise, for compounds of type (iii), crosslinked polyamines having the formula $(PA)_w(T)_x$ may be combined with from about 0.05, preferably from about 0.3 parts by weight of an L unit to about 2 parts by weight of an L unit to form a suitable modified polyamine compound having the formula $[(PA)_w(T)_x]_y[L]_z$.

Polyamine Backbone (PA Units)

The modified polyamine compounds of the present invention comprise a Polyamine Backbone, PA unit, which can be optionally, but preferably grafted. The following are non-limiting examples of suitable PA units according to the present invention.

Polyalkyleneimine

A preferred PA unit according to the present invention are polyalkyleneimines and polyalkyleneamines having the general formula:

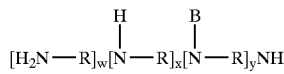

wherein R is $C_2$–$C_{12}$ linear alkylene, $C_3$–$C_{12}$ branched alkylene, and mixtures thereof preferably R is ethylene, 1,3-propylene, and 1,6-hexylene, more preferred is ethylene; B representing a continuation of the chain structure by branching. The indices w, x, and y are such that the molecular weight of said polyamines is from about 50,000 Daltons to about 15,000,000 Daltons, more preferably from about 350,000 Daltons to about 15,000,000 Daltons, even more preferably still from about 600,000 Daltons to about 15,000,000 Daltons. The index w typically has the value of y+1. PA units may be used as crude products or mixtures, and if desired by the formulator, these PA units may be used in the presence of small amounts of diamines as described herein above, wherein the amount of diamines, inter alia, ethylene diamine, hexamethylene diamine may be present up to about 10% by weight, of the PA unit mixture.

Co-polymeric Polyamines

Another example of a preferred PA unit according to the present invention are the polyvinyl amine homo-polymers or co-polymers having the formula:

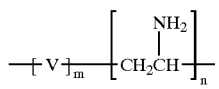

wherein V is a co-monomer, non-limiting examples of which include vinyl amides, vinyl pyrrolidone, vinyl imidazole, vinyl esters, vinyl alcohols, and mixtures thereof, all of which can be taken together or in combination with polyvinyl amine to form suitable co-polymerization products suitable for use in the soil entrainment system of the present invention.

The indices w, x, y, m(when present), and n, when present, are such that the molecular weight of said polyamines is from about 50,000 Daltons to about 15,000,000 Daltons, more preferably from about 350,000 Daltons to about 15,000,000 Daltons, even more preferably still from about 600,000 Daltons to about 15,000,000 Daltons.

Polyamine Backbone Modifications

Optionally, but preferably, the PA units of the present invention are modified either before or after reaction with a T unit or L unit crosslinking agent. The two preferred types of modifications are grafting and capping.

Preferably the PA units of the present invention are grafted, that is the PA unit is further reacted with a reagent which elongates said PA unit chain, preferably by reaction of the nitrogens of the PA backbone unit with one or more equivalents of aziridine (ethyleneimine), caprolactam, and mixtures thereof. Grafting units, in contrast to the "capping" units described herein below, can further react on themselves to provide PA unit chain propagation. An example of a preferred grafted PA unit of the present invention has the formula:

wherein R, B, w, x, and y are the same as defined herein above and G is hydrogen or an extension of the PA unit backbone by grafting. Non-limiting examples of preferred grafting agents are aziridine (ethyleneimine), caprolactam, and mixtures thereof. A preferred grafting agent is aziridine wherein the backbone is extended by units having the formula:

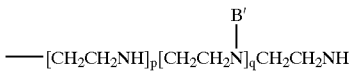

wherein B' is a continuation by branching wherein the graft does not exceed about 12 units, preferably —$CH_2CH_2NH_2$ and the value of the indices p+q have the value from 0, preferably from about 1, more preferably from about 2 to about 7, preferably to about 5. Another preferred grafting unit is caprolactam.

The PA units of the present invention can be grafted prior to or after crosslinking with one or more T units described herein below, preferably the grafting is accomplished after crosslinking with said T unit. This allows the formulator to take advantage of the differential reactivity between the primary and secondary amino units of the PA unit backbone thereby allowing the formulator to controllably link said PA units and to also control the amount of subsequent branching which results from the grafting step.

Another optional but preferred PA unit modification is the presence of "capping" units. For example, a PA unit is reacted with an amount of a monocarboxylic acid, non-limiting examples of which are $C_1$–$C_{22}$ linear or branched alkyl, preferably $C_{10}$–$C_{18}$ linear alkyl, inter alia, lauric acid, myristic acid. The amount of capping unit which is reacted with the PA unit is an amount which is sufficient to achieve the desired properties of the formula. However, the amount of capping unit used is not sufficient to abate any further crosslinking or grafting which the formulator may choose to perform.

Crosslinking Units

Amide-forming T Crosslinking Units

T crosslinking units are preferably carbonyl comprising polyamido forming units. The T units are taken together with PA units to form crosslinked modified polyamine compounds having the formula $(PA)_w(T)_x$ or $[(PA)_w(T)_x]_y[L]_z$.

A preferred embodiment of the present invention includes crosslinked PA units wherein a T unit provides crosslinking between two or more PA units to form a $(PA)_w(T)_x$ polyamido crosslinked section. A preferred crosslinking T unit has the general formula:

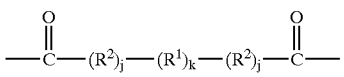

wherein $R^1$ is methylene, phenylene, and mixtures thereof; preferably methylene. The index k has the value from 2 to about 8, preferably to about 4. Preferred values of k are 2, 3, and 4. $R^2$ is —NH— thereby forming a urethane amide linkage when said $R^2$ comprising T units react with the backbone nitrogens of the PA units. The value of the index j is independently 0 or 1. The presence of $R^2$ units can result, for example, from the use of diisocyanates as crosslinking agents. Non-limiting examples of dibasic acids which are used as a source for T units in the above formula include succinic acid, maleic acid, adipic acid, glutaric acid, suberic acid, sebacic acid, and terephthalic acid. However, the formulator is not limited to crosslinking T units deriving from dibasic acids, for example, tribasic crosslinking T units, inter alia, citrate, may be used to link the PA units of the present invention.

Examples of $(PA)_w(T)_x$ compounds according to the present invention are obtained by condensation of dicarboxylic acids, inter alia, succinic acid, maleic acid, adipic acid, terephthalic acid, with polyalkylene polyamines, inter alia, diethylenetriamine, triethylenetetramine, dipropylenetriamine, tripropylenetetramine wherein the ratio of the dicarboxylic acid to polyalkyleneamine is from 1:0.8 to 1:1.5 moles, preferably a ratio of from 1:0.9 to 1:1.2 moles wherein the resulting crosslinked material has a viscosity in a 50% by weight, aqueous solution of more than 100 centipoise at 25° C.

Non-amide Forming L Crosslinking Units

Another preferred embodiment of the polyamines of the present invention are $(PA)_w(T)_x$ units which are further crosslinked by L units to form polyamido amines having the formula $[(PA)_w(T)_x]_y[L]_z$ or are reacted with PA units to form non-amide polyamines having the formula $(PA)_w(L)_z$.

The L units of the present invention are any unit which suitably crosslinks PA units or $(PA)_w(T)_x$ units. Preferred L linking units comprise units which are derived from the use of epihalohydrins, preferably epichlorohydrin, as a crosslinking agent. The epihalohydrins can be used directly with the PA units or suitably combined with other crosslinking adjuncts non-limiting examples of which include alkyleneglycols, and polyalkylene polyglycols, inter alia, ethylene glycol, diethylene glycol, polyethylene glycol, propylene glycol, dipropylene glycol, polypropylene glycol, butylene glycol, hexanediol-1,6-glycerol, oligoglycerol, pentaerythrites, polyols which are obtained by the reduction of carbohydrates (sorbitol, mannitol), monosaccharides, disaccharides, oligosaccharides, polysaccharides, polyvinyl alcohols, and mixtures thereof.

For example, a suitable L unit is a dodecylene unit having the formula:

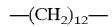

wherein an equivalent of 1,12-dichlorododecane is reacted, for example, with a suitable amount of a PA unit to produce a polyamine which is crosslinked via dodecylene units. For the purposes of the present invention, L crosslinking units which comprise only carbon and hydrogen are considered to be "hydrocarbyl" L units. Preferred hydrocarbyl units are polyalkylene units have the formula:

wherein n is from 1 to about 50.

Hydrocarbyl L units may be derived from hydrocarbons having two units which are capable of reacting with the nitrogen of the PA units. Non-limiting examples of precursors which result in the formation of hydrocarbyl L units include 1,6-dibromohexane, 1,8-ditosyloctane, and 1,4-dichlorotetradecane.

Further examples of preferred non-amide forming crosslinking L units are the units which derive from crosslinking units wherein epihalohydrin is used as the connecting unit. For example, 1,12-dihydroxydodecane is reacted with epichlorohydrin to form the bis-epoxide non-amide forming L unit precursor having the formula:

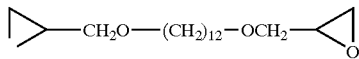

which when reacted with one or more PA units or $(PA)_w(T)_x$ units results in an L crosslinking unit having the formula:

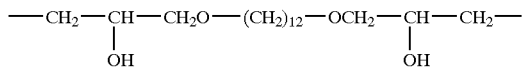

however, it is not necessary to pre-form and isolate the bis-epoxide, instead the crosslinking unit precursor may be formed in situ by reaction of 1,12-dihydroxydodecane or other suitable precursor unit with epihalohydrin in the presence of grafted or ungrafted PA units or $(PA)_w(T)_x$ units.

Other crosslinking L units which utilize one or more epihalohydrin connecting units include polyalkyleneoxy L units having the formula:

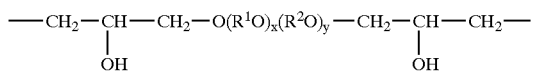

wherein $R^1$ is ethylene, $R^2$ is 1,2-propylene, x is from 0 to 100 and y is from 0 to 100.

Another preferred unit which can comprise an L unit and which can be suitably combined with epihalohydrin connecting units include polyhydroxy units having the formula:

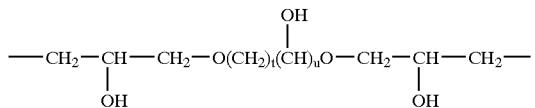

wherein the index t is from at least 2 to about 20 and the index u is from 1 to about 6. The formulator may also combine units to form hybrid L crosslinking units, for example, units having the formula:

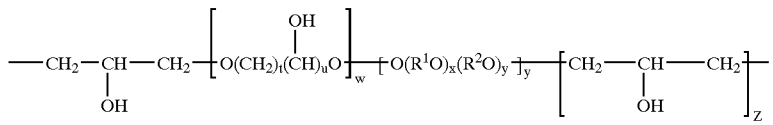

wherein the indices w and y are each independently from 1 to 50, z is units are present in a sufficient to suitably connect the polyhydroxy units and the polyalkyleneoxy units into the backbone without the formation of ether linkages.

The following is an example of an L linking group which comprises both a polyalkyleneoxy and a polyhydroxy unit:

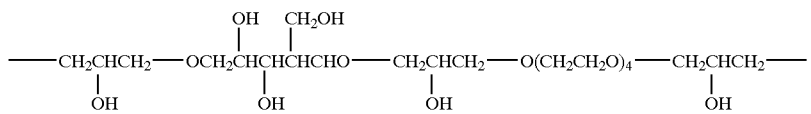

A further example of a preferred crosslinking L units are units which comprises at least two aziridine groups as connecting groups, for example an L unit having the formula:

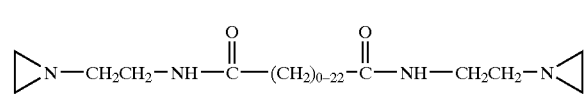

which can be used to link two $(PA)_w$ units, two $(PA)_w(T)_x$ units, or mixtures thereof.

The polyamines of the present invention may have varying final compositions, for example, $(PA)_w(T)_x$, $[(PA)_w(T)_x]_y[L]_z$, $[(PA)]_w[L]_z$, and mixtures thereof, wherein each PA unit may be grafted or ungrafted. The indices w and x have values such that the ratio of w to x is from 0.8:1 to 1.5:1; y and z have values such that said polyamido compound comprises from about 0.05, preferably to about 0.3 to 2 parts by weight of said L unit. In the cases wherein no crosslinking takes place the indices w and y will be equal to 1 and x and z will be equal to 0. In the case wherein no crosslinking occurs using L units, the index y is equal to 1 and z is equal to 0. In the case wherein no crosslinking occurs using T units, the indices w and y are equal to 1 and x is equal to 0.

A preferred embodiment of the present invention which comprises PA units, T units, and L units includes the reaction product of:
  a) 1 part by weight, of a polyamine obtained by condensation of 1 mole of a dicarboxylic acid with a polyalkylene polyamine (i.e., diethylenetriamine) to the extent wherein at least about 10% of the —NH backbone hydrogens are unmodified by reaction with said dicarboxylic acid, then optionally reacting the obtained polyamine condensation product with up to 12 ethyleneimine units (i.e., grafting of the backbone using aziridine) per basic nitrogen atom; and
  b) further reacting the product obtained in (a) with from 0.05, preferably from about 0.3 to about 2 parts by weight, of an L units, inter alia, the reaction product of a polyalkylene oxide having from 8 to 100 alkylene oxide units with epichlorohydrin at a temperature of from about 20° C. to about 100° C.

Another preferred embodiment of the nitrogen-containing polymers useful in the present invention includes the reaction product of:

a) 1 part by weight, of a polyamidoamine obtained by condensation of 1 mole of a dicarboxylic acid with from about 0.8 to about 1.5 moles of a polyalkylene polyamine then optionally reacting the obtained polyamidoamine condensation product with up to 8 ethyleneimine units per basic nitrogen atom; and b) further reacting the product obtained in (a) with from about 0.05 to about 2 parts by weight of the reaction product of a polyalkylene oxide having from 8 to 100 alkylene oxide units with epichlorohydrin at a temperature of from about 20° C. to about 100° C.

A preferred embodiment of the present invention are the water-soluble condensation products which can be obtained by the reaction of:
  a) polyalkyleneimines and polyalkyleneimines grafted with ethyleneimines, and mixtures thereof; with
  b) at least bifunctional halogen-free cross-linking agents, said agents selected from the group consisting of:
    i) ethylene carbonate, propylene carbonate, urea, and mixtures thereof;
    ii) mono-carboxylic acids comprising one olefin moiety, inter alia, acrylic acid, methacrylic acid, crotonic acid; and the esters, amides, and anhydrides thereof; polycarboxylic acids, inter alia, oxalic acid, succinic acid, tartaric acid, itaconic acid, maleic acid; and the esters, amides, and anhydrides thereof;
    iii) reaction products of polyetherdiamines, alkylenediamines, polyalkylene-diamines, and mixtures thereof, with mono-carboxylic acids comprising one olefin moiety wherein the resulting polyamine comprises a functional units which is selected from the group consisting of at least two ethylenically unsaturated double bonds, carbonamide, carboxyl group, ester group, and mixtures thereof;
    iv) at least two aziridine group-containing reaction products of dicarboxylic acid esters with ethyleneimine and mixtures of the cross-linking agents.

However, prior to reaction of $(PA)_w(T)_x$ units formed herein above, the $(PA)_w(T)_x$ polyamine compound may be partially amidated ("capped" as described herein above) by treatment with a mono carboxylic acid or the esters of mono carboxylic acids. The formulator may vary the degree to which the backbone nitrogens are amidated according to the desired properties of the final soil entrainment system. Non-limiting examples of suitable mono-carboxylic acids include formic acid, acetic acid, propionic acid, benzoic acid, salicylic acid, lauric acid, palmitic acid, stearic acid, oleic acid, linoleic acid, behenic acid, and mixtures thereof.

The high molecular weight modified polyamine condensation products of the present invention (also referred to herein as "resins") are preferably formed from the reaction of one or more grafted, cross-linked polyethyleneimines and one or more polyethylene and/or polypropylene glycol copolymers, wherein the resulting crosslinked modified polyamines (resins) have a final viscosity of more than or equal to 300 mPa-sec., preferably from 400 to 2,500 mPa-sec. when measured at 20° C. in a 20% aqueous solution. The modified polyamine compounds of the present invention are suitably described in U.S. Pat. No. 3,642,572 Eadres et al., issued Feb. 15, 1972, U.S. Pat. No. 4,144,123 Scharf et al., issued Mar. 13, 1979 and U.S. Pat. No. 4,371,674 Hertel et al., issued Feb. 1, 1983, NE 6,612,293, DT 1,946, 471, DT 36386, DT 733,973, DE 1,771,814, all of which are incorporated herein by reference. Examples of preferred modified polyamines useful as nitrogen-containing polymers herein are branched polyethyleneimines with a molecular weight of about 25,000 Daltons, and Lupasol® SK and Lupasol® SK(A) available from BASF.

C. SURFACTANTS

Surfactants useful in the present compositions will typically be selected from those which are generally used in hard surface cleaning. The surfactant is preferably selected from the group consisting of anionic, nonionic, zwitterionic, cationic, amphoteric and mixtures thereof.

Cationic surfactants, for purposes of the present invention, do not include compounds described as cationic antimicrobial actives in Section I.A. supra. More preferably, the surfactant is a nonionic surfactant. In preferred embodiments, the present compositions are essentially free of, or free of, anionic surfactant, zwitterionic surfactant, and/or amphoteric surfactant.

The antimicrobial, hard surface cleaning compositions of the present invention contain one or more detergent surfactants. It is preferred that these surfactants are selected from the group consisting of anionic, nonionic, zwitterionic, cationic, amphoteric and mixtures thereof. More preferably the detergent surfactant is uncharged and has a linear or branched structure and is a nonionic detergent surfactant. Preferred anionic and nonionic detergent surfactants have hydrophobic chains containing from about 8 to about 18, preferably from about 8 to about 15, carbon atoms. Examples of suitable anionic surfactants include, but are not limited to, linear alkyl sulfates, alkyl sulfonates, and the like. Examples of suitable nonionic surfactants include alkylethoxylates and the like. Examples of zwitterionic surfactants include betaines and sulfobetaines. Examples of amphoteric surfactants include alkylampho glycinates, and alkyl imino propionate. Further examples of suitable surfactants are described in McCutcheon's Vol. 1: Emulsifiers and Detergents, North American Ed., McCutheon Division, MC Publishing Co., 1995, which is incorporated herein by reference.

One class of preferred nonionic surfactant is alkyl ethoxylates. The alkyl ethoxylates of the present invention are either linear or branched, and contain from about 8 carbon atoms to about 14 carbon atoms, and from about 4 ethylene oxide units to about 25 ethylene oxide units. Examples of alkyl ethoxylates include Neodol® 91-6, Neodol 91-8® supplied by the Shell Corporation (P.O. Box 2463, 1 Shell Plaza, Houston, Tex.), and Alfonic® 810-60 supplied by Vista Corporation, (900 Threadneedle P.O. Box 19029, Houston, Tex.). More preferred surfactants are the alkyl ethoxylates comprising from about 9 to about 12 carbon atoms, and from about 4 to about 8 ethylene oxide units. These surfactants offer excellent cleaning benefits and work synergistically with the required hydrophilic polymers. A most preferred alkyl ethoxylate is $C_{11}EO_5$, available from the Shell Chemical Company under the trade name Neodol® 1-5.

Alternative nonionic detergent surfactants for use herein are alkoxylated alcohols generally comprising from about 6 to about 16 carbon atoms in the hydrophobic alkyl chain of the alcohol. Typical alkoxylation groups are propoxy groups or propoxy groups in combination with ethoxy groups. Such compounds are commercially available under the tradename Antarox® available from Rhodia (CN 7500, Cranberry, N.J.). with a wide variety of chain length and alkoxylation degrees. Block copolymers of ethylene oxide and propylene oxide can also be used and are available from BASF under the trade name Pluronic®. Preferred nonionic detergent surfactants for use herein are according to the formula $R(X)_nH$, were R is an alkyl chain having from about 6 to about 16 carbon atoms, preferably from about 9 to about 16, X is a propoxy, or a mixture of ethoxy and propoxy groups, n is an integer of from about 4 to about 30, preferably from about 5 to about 10. Particularly preferred nonionic surfactants of this class include Nonidet™ SF-3 and Nonidet™ SF-S surfactants. Other non-ionic surfactants that can be used include those derived from natural sources such as sugars and include $C_8$–$C_{16}$ N-alkyl glucose amide surfactants.

Another type of preferred nonionic surfactant are the alkylpolysaccharides that are disclosed in U.S. Pat. No. 5,776,872, issued Jul. 7, 1998 to Giret et al.; U.S. Pat. No. 5,883,059, issued Mar. 16, 1999 to Furman et al.; U.S. Pat. No. 5,883,062, issued Mar. 16, 1999 to Addison et al.; and U.S. Pat. No. 5,906,973, issued May 25, 1999 to Ouzounis et al.; which are all incorporated by reference herein.

Suitable alkylpolysaccharides for use herein are disclosed in U.S. Pat. No. 4,565,647, Llenado, issued Jan. 21, 1986, incorporated by reference herein, having a hydrophobic group containing from about 6 to about 30 carbon atoms, preferably from about 10 t6 about 16 carbon atoms and a polysaccharide, e.g., a polyglycoside, hydrophilic group. For acidic or alkaline cleaning compositions/solutions suitable for use in no-rinse methods, the preferred alkyl polysaccharide preferably comprises a broad distribution of chain lengths, as these provide the best combination of wetting, cleaning, and low residue upon drying. This "broad distribution" is defined by at least about 50% of the chainlength mixture comprising from about 10 carbon atoms to about 16 carbon atoms. Preferably, the alkyl group of the alkyl polysaccharide consists of a mixtures of chainlength, preferably from about 6 to about 18 carbon atoms, more preferably from about 8 to about 16 carbon atoms, and hydrophilic group containing from about one to about 1.5 saccharide, preferably glucoside, groups per molecule. This "broad chainlength distribution" is defined by at least about 50% of the chainlength mixture comprising from about 10 carbon atoms to about 16 carbon atoms. A broad mixture of chain lengths, particularly $C_8$–$C_{16}$, is highly desirable relative to narrower range chain length mixtures, and particularly versus lower (i.e., $C_8$–$C_{10}$ or $C_8$–$C_{12}$) chainlength alkyl polyglucoside mixtures. It is also found that the preferred $C_{8-16}$ alkyl polyglucoside provides much improved perfume solubility versus lower and narrower chainlength alkyl polyglucosides, as well as other preferred surfactants, including the $C_8$–$C_{14}$ alkyl ethoxylates. Any reducing saccharide containing 5 or 6 carbon atoms can be used, e.g., glucose, galactose and galactosyl moieties can be substituted for the glucosyl moieties. (optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units. The glycosyl is preferably derived from glucose.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from 8 to 18, preferably from 10 to 16, carbon atoms. Preferably, the alkyl group is a straight-chain saturated alkyl group. The alkyl group can contain up to about 3 hydroxyl groups and/or the polyalkyleneoxide chain can contain up to about 10, preferably less than 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides and/ or galatoses. Suitable mixtures include coconut alkyl, di-, tri-, tetra-, and pentaglucosides and tallow alkyl tetra-, penta- and hexaglucosides.

To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-,3-, 4- and/or 6-position, preferably predominantly the 2-position.

In the alkyl polyglycosides, the alkyl moieties can be derived from the usual sources like fats, oils or chemically produced alcohols while their sugar moieties are created from hydrolyzed polysaccharides. Alkyl polyglycosides are the condensation product of fatty alcohol and sugars like glucose with the number of glucose units defining the relative hydrophilicity. As discussed above, the sugar units can additionally be alkoxylated either before or after reaction with the fatty alcohols. Such alkyl polyglycosides are described in detail in WO 86/05199 for example. Technical alkyl polyglycosides are generally not molecularly uniform products, but represent mixtures of alkyl groups and mixtures of monosaccharides and different oligosaccharides. Alkyl polyglycosides (also sometimes referred to as "APG's") are preferred for the purposes of the invention since they provide additional improvement in surface appearance relative to other surfactants. The glycoside moieties are preferably glucose moieties. The alkyl substituent is preferably a saturated or unsaturated alkyl moiety containing from about 8 to about 18 carbon atoms, preferably from about 8 to about 10 carbon atoms or a mixture of such alkyl moieties. $C_8$–$C_{16}$ alkyl polyglucosides are commercially available (e.g., Simusol® surfactants from Seppic Corporation, 75 Quai d'Orsay, 75321 Paris, Cedex 7, France, and Glucopon® 425 available from Henkel. However, it has been found that purity of the alkyl polyglucoside can also impact performance, particularly end result for certain applications, including daily shower product technology. In the present invention, the preferred alkyl polyglucosides are those which have been purified enough for use in personal cleansing. Most preferred are "cosmetic grade" alkyl polyglucosides, particularly $C_8$ to $C_{16}$ alkyl polyglucosides, such as Plantaren 2000®, Plantaren 2000 N®, and Plantaren 2000 N UP®, available from Henkel Corporation (Postfach 101100, D 40191 Dusseldorf, Germany).

Suitable anionic surfactants typically comprise a hydrophobic chain containing from about 8 carbon atoms to about 18, preferably from about 8 to about 16, carbon atoms, and typically include a sulfonate or carboxylate hydrophilic head group.

Suitable anionic surfactants include the $C_8$–$C_{18}$ alkyl sulfonates, $C_{10}$–$C_{14}$ linear or branched alkyl benzene sulfonates, $C_{10-14}$ alkyl sulfates and ethoxysulfates (e.g., Stepanol AM® from Stepan)., $C_9$–$C_{15}$ alkyl ethoxy carboxylates (Neodox® surfactants available from Shell Chemical Corporation),. Suitable commercially available sulfonates are available from Stepan under the tradename Bio-Terge PAS-8® as well as from the Witco Corporation under the tradename Witconate NAS-8®, and Hostapur SAS® from Hoechst, Aktiengesellschaft, D-6230 Frankfurt, Germany.

Also suitable for use in the present invention are the fluorinated nonionic surfactants. One particularly suitable fluorinated nonionic surfactant is Fluorad® F 170 (3M). Fluorad® F 170 has the formula:

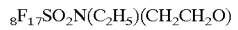
$_8F_{17}SO_2N(C_2H_5)(CH_2CH_2O)$

Also suitable for use in the present invention are silicone containing surfactants. One example of these types of surfactants is Silwet L7604 available from Union Carbide.

Some of the more preferred commercially available surfactants include Neodol™ 11-5, Nonidet™ SF-3, Nonidet™ SF-5, (all Shell Chemical), $C_8$ sulfonate (Witconate NA-8) $C_{11-18}$ APG (Henkel), and Fluorad® F170 (3M).

In general, the antimicrobial, hard surface cleaning compositions of the present invention comprise surfactant, preferably nonionic surfactant, at a level of from about 0.001% to about 15%, preferably from about 0.01% to about 7%, and more preferably from about 0.01% to about 1%, by weight of the composition.

In preferred low-surfactant compositions for use in no-rinse cleaning methods, such compositions typically comprise surfactant, preferably nonionic surfactant, at a level of from about 0.005% to about 0.5%, preferably from about 0.005% to about 0.3%, and more preferably from about 0.005% to about 0.1%, by weight of the composition.

D. OPTIONAL INGREDIENTS

1. Aqueous Carrier

The compositions of the present invention can also comprise an aqueous liquid carrier that comprises water and optionally one or more solvents. The aqueous carrier typically comprises from about 50% to about 100%, preferably from about 60% to about 98%, and more preferably from about 80% to about 96%, by weight of the aqueous carrier, of water and from about 0% to about 50%, preferably from about 0.5% to about 30%, and more preferably from about 1% to about 20%, by weight of the aqueous carrier, of optional solvent.

In general, the antimicrobial, hard surface cleaning compositions of the present invention comprise aqueous carrier at a level of from about 50% to about 99.99%, preferably from about 60% to about 90%, and more preferably from about 90% to about 99.99%, by weight of the composition.

In preferred low-surfactant compositions for use in no-rinse cleaning methods, such compositions typically comprise aqueous carrier at a level of from about 98% to about 99.99%, preferably from about 99% to about 99.99%, and more preferably from about 99.5% to about 99.99%, by weight of the composition.

It is preferred that any water in the composition, such as in premixed or ready to use solutions, is deionized or softened water. However, conventional tap water can be used.

The surfactant provides cleaning and/ or wetting even without a cleaning solvent present. However, the cleaning can normally be further improved by the use of the right solvent. By solvent, it is meant an agent which assists the surfactant to remove soils such as those commonly encountered in the home. The solvent also can participate in the building of viscosity, if needed, and in increasing the stability of the composition.

Such solvents typically have a terminal $C_3$–$C_6$ hydrocarbon attached to from one to three ethylene glycol or propylene glycol moieties to provide the appropriate degree of hydrophobicity and, preferably, surface activity. Examples of commercially available hydrophobic cleaning solvents based on ethylene glycol chemistry include mono-ethylene glycol n-hexyl ether (Hexyl Cellosolve® available from Union Carbide). Examples of commercially available hydrophobic cleaning solvents based on propylene glycol chemistry include the di-, and tri-propylene glycol derivatives of propyl and butyl alcohol, which are available from Arco Chemical, 3801 West Chester Pike, Newtown Square, Pa. 19073) and Dow Chemical (1691 N. Swede Road, Midland, Mich.) under the trade names Arcosolv® and Dowanol®.

In the context of the present invention, preferred solvents are selected from the group consisting of mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, methanol, ethanol, isopropanol, n-butanol, iso-butanol, pentanol, 2-methyl-1-butanol, 2-butanone, methoxymethanol, methoxyethanol, methoxy propanol, ethoxypropanol, propoxypropanol, ethoxybutanol and mixtures thereof. "Butyl" includes both normal butyl, isobutyl and tertiary butyl groups. More prefered solvents include ethanol, propanol, propoxypropanol, mono-propylene glycol and mono-propylene glycol mono-butyl ether. The latter two are available under the tradenames Dowanol DPnP® and Dowanol DPnB®. Di-propylene glycol mono-t-butyl ether is commercially available from Arco Chemical under the tradename Arcosolv PTB®.

The amount of solvent can vary depending on the amount of other ingredients present in the composition. The solvent is normally helpful in providing good cleaning, such as in floor cleaner applications.

2. Buffer

An optional buffering agent may be an active detergent in its own right, or it may be a low molecular weight, organic or inorganic material that is used in this composition solely for maintaining the desired pH. The buffer can be alkaline, acidic or neutral. Preferred buffering agents for compositions of this invention are nitrogen-containing materials. Some examples are amino acids such as lysine or lower alcohol amines like mono-, di-, and tri-ethanolamine. Other preferred nitrogen-containing buffering agents are Tri (hydroxymethyl)amino methane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris(hydroxymethyl)methyl glycine (tricine). Other suitable buffers include ammonium carbamate, citric acid, acetic acid. Mixtures of any of the above are also acceptable. Useful inorganic buffers/alkalinity sources include ammonia, the alkali metal carbonates and alkali metal phosphates, e.g., sodium carbonate, sodium polyphosphate. For additional buffers see McCutcheon's EMULSIFIERS AND DETERGENTS, North American Edition, 1997, McCutcheon Division, MC Publishing Company Kirk and WO 95/07971 both of which are incorporated herein by reference.

Preferred buffers include, but are not limited to, ammonia, methanol amine, ethanol amine, 2-amino-2-methyl-1-propanol, 2-dimethylamino-2-methyl-1-propanol, 1,3-bis (methylamine)-cyclohexane, acetic acid, glycolic acid and the like. Most preferred among these are ammonia, 1,3-bis (methylamine)-cyclohexane, 2-dimethylamino-2-methyl-1-propanol and acetic acid.

In one preferred aspect the composition of the present invention wherein to minimize streaking/filming problems, the buffering is provided, at least in part, by volatile materials whose molecular weight is less than about 400 g/mole.

If buffer is desirable for cleaning performance, the present compositions will preferably contain at least about 0%, more preferably at least about 0.001%, even more preferably still, at least about 0.01% by weight of the composition of buffering agent. The composition will also preferably contain no more than about 1%, more preferably no more than about 0.75%, even more preferably, no more than about 0.5% by weight of the composition of buffering agent.

3. Perfume

Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise from about 0.005% to about 2%, by weight, of the antimicrobial, hard surface cleaning compositions herein, and individual perfumery ingredients can comprise from about 0.0001% to about 90% of a finished perfume composition.

When present, the perfume comprises from about 0% to about 0.5%, more preferably from about 0.001% to about 0.1%, even more preferably still 0.005% to about 0.08%, by weight of the composition.

4. Suds Suppressor

The composition of the present invention can optionally contain a suds suppressor. When present the suds suppressor is preferably present from about 0.0005% to about 0.01%, more preferably from about 0.001% to about 0.005%, by weight of the composition.

Suitable suds suppressors include, silicone suds suppressor such as silicone polymers and linear or branched $C_{10}$–$C_{18}$ fatty acids or alcohols, with silicone suds suppressor being preferred. One suitable suds supressor is Dow Corning Silicone Suds Supressor.

Another suitable suds suppressors is a mixture of Polyethylene glycol stearate (4% Wt, CAS #9004993); Methylated silica (2% Wt, CAS #67762907); Octamethyl cyclotetrasiloxane (2% Wt, CAS #556672), available from Dow Corning.

Further examples of suitable suds suppressors can be found in co-pending U.S. patent application Ser. No. 09/381,550 filed Sep. 20, 1999 by R. A. Masters et al. (P&G Case 6555), which is incorporated herein by reference.

Other optional ingredients in the present compositions include colorants or dyes, and the like.

II. KITS FOR CLEANING HARD SURFACES

In another aspect of the present invention a kit is provided for. This kit can have an assembly of one or more units, either packaged together or separately. For example, the kit can include a pad or a dry wipe with cleaning solution. A second example is a kit with pad or dry wipe, implement and solution. A third example is a kit with concentrated refill, ready to use solution and pads with superabsorbent material. This kit comprises an implement containing a pad containing superabsorbent material and a detergent composition that provides effective cleaning and good particulate soil removal when used with a disposable cleaning pad and without rinsing comprising an effective amount of an soil entrainment system.

It is preferred that the implement comprises:
a. a handle; and
b. a removable cleaning pad preferably containing an effective amount of a superabsorbent material, and having a plurality of substantially planar surfaces, wherein each of the substantially planar surfaces contacts the surface being cleaned, more preferably said pad is a removable cleaning pad having a length and a width, the pad comprising i. a scrubbing layer; and
ii. an absorbent layer comprising a first layer and a second layer, where the first layer is located between the scrubbing layer and the second layer (i.e., the first layer is below the second layer) and has a smaller width than the second layer.

An important aspect of the cleaning performance provided by the preferred pad is related to the ability to provide multiple planar surfaces that contact the soiled surface during the cleaning operation. In the context of a cleaning implement such as a mop, these planar surfaces are provided such that during the typical cleaning operation (i.e., where the implement is moved back and forth in a direction substantially perpendicular to the pad's width), each of the planar surfaces contact the surface being cleaned as a result of "rocking" of the cleaning pad.

In one preferred aspect of the present invention, the kit further contains instructions for use of the kit which are in association with the composition and the implement to insure optimum usage. In a further preferment of this aspect, these instructions are on the back of the pad in the form of words and/or pictures and explain which side of the pad to attach to the implement.

In one preferred aspect of the implement the pad is detachably mounted on the implement. That is, the pad can be removed and replaced by another pad. This is especially useful, when the pad is excessively soiled. The pad can be removed and replaced with a fresh clean pad.

In another preferred aspect the implement further comprises a dosing device. The dosing device delivers the detergent composition to the surface to be cleaned. This dosing device can be battery powered, electrically powered, or hand powered (that is the user works the dosing device, such as a pump manually). It is more preferred that the dosing device be battery or electrically powered and includes a dispensing trigger or button. It is even more preferred that when the dosing device is battery or electrically powered, it applies a continuous flow to the surface to be cleaned.

In another preferred aspect the implement further comprises a reservoir which holds the cleaning solution. It is preferred that, when present, the reservoir is detachably mounted on the implement. It is even more preferred that when implement comprises a detachably mounted reservoir that the implement also comprises a dosing device, even more preferably a battery or electrically powered dosing device.

In one preferred aspect the pad comprises an inner absorbent core with super-absorbent polymer and outer scrub layer made of an apertured form film.

One of ordinary skill in the art can select various materials that can be utilized to prepare the disposable pads and/or implements herein. Thus, while preferred materials are described herein for the various implement and cleaning pad components, it is recognized that the scope of operable materials is not limited to such disclosures.

More details on suitable cleaning pads (such as those which include superabsorbent material), implements, and the components of the implements, such as the removable cleaning pad, handle etc., can be found in co-pending U.S. patent applications Ser. Nos. 08/756,774, filed Nov. 26, 1996 by V. S. Ping, et al. (P&G Case 6383), and Ser. No. 08/716,755, filed Sep. 23, 1996 by A. J. Irwin (P&G Case 6262), Ser. No. 60/061,296, filed Oct. 7, 1997 by N. J. Policicchio, et al. (P&G Case 6873P), Ser. No. 09/037,379, filed Mar. 10, 1998 by R. A. Masters, et al. (P&G Case 6553), Ser. No. 60/041,273, filed Mar. 20, 1997 by R. A.

Masters, et al. (P&G Case 6555P), Ser. No. 60/045,858, filed May 8, 1997 by R. A. Masters, et al. (P&G Case 6555P2), Ser. No. 60/085,837, filed May 18, 1998 (P&G Case 7159P), Ser. No. 08/756,999, filed Nov. 26, 1996 (P&G Case 6269R), Ser. No. 08/756,864, filed Nov. 26, 1996 (P&G Case 6270R), Ser. No. 08/756,616, filed Nov. 26, 1996 (P&G Case 6382), Ser. No. 08/756,774, filed Nov. 26, 1996 (P&G Case 6383), Ser. No. 08/756,151, filed Nov. 26, 1996 (P&G Case 6384), Ser. No. 08/756,997, filed Nov. 26, 1996 (P&G Case 6385), Ser. No. 08/756,998, filed Nov. 26, 1996 (P&G Case 6386), Ser. No. 08/756,507, filed Nov. 26, 1996 (P&G Case 6387), Ser. No. 09/188,604, filed Nov. 9, 1998 (P&G Case 7337), 60/110,356, filed Dec. 1, 1998 K. W. Willman, et al. (P&G Case 7367P), Ser. No. 60/110,476, filed Dec. 1, 1998 N. J. Policicchio, et al. (P&G Case 7368P), Ser. No. 09/201,620 filed Nov. 30, 1998, accepted May 25, 1999 (P&G Case 7362), and Ser. No. 09/290,960, filed Apr. 13, 1999 (P&G Case 7497), all of which are incorporated herein by reference. More specific details on implements, and the components of the implements, such as the removable cleaning pad, handle etc., can be found in co-pending U.S. Design Pat. Applications Serial Nos. 29/097,135, filed Nov. 30, 1998 (P&G Case D605), 29/097, 132, filed Nov. 30, 1998 (P&G Case D603), and Ser. No. 29/097,585, filed Dec. 12, 1998 (P&G Case D610), all of which are incorporated herein by reference. See also WO applications Nos. 98/11813, and 98/42819, both of which are incorporated herein by reference.

Cleaning Pads

The cleaning pads will preferably have an absorbent capacity, when measured under a confining pressure of 0.09 psi after 20 minutes (1200 seconds) (hereafter referred to as "$t_{1200}$ absorbent capacity"), of at least about I g deionized water per g of the cleaning pad, preferably at least about 5 g deionized water per g of the cleaning pad, and more preferably at least about 10 g deionized water per g of the cleaning pad. The absorbent capacity of the pad is measured at 20 minutes (1200 seconds) after exposure to deionized water, as this represents a typical time for the consumer to clean a hard surface such as a floor. The confining pressure represents typical pressures exerted on the pad during the cleaning process. As such, the cleaning pad should be capable of absorbing significant amounts of the cleaning solution within this 1200 second period under 0.09 psi. The cleaning pad will preferably have a $t_{1200}$ absorbent capacity of at least about 15 g/g, more preferably at least about 20 g/g, still more preferably at least about 25 g/g and most preferably at least about 30 g/g. The cleaning pad will preferably have a tgoo absorbent capacity of at least about 10 g/g, more preferably a tgoo absorbent capacity of at least about 20 g/g.

Values for $t_{1200}$ and tgoo absorbent capacity are measured by the performance under pressure (referred to herein as "PUP") method, which is described in detail in the Test Methods section in allowed application Ser. No. 08/756,507, Holt, Masters, and Ping, filed Nov. 26, 1996, said application being incorporated herein, in its entirety, by reference. The application contains a more complete disclosure of the pads, instruments, etc. that are of use herein.

The cleaning pads will also preferably, but not necessarily, have a total fluid capacity (of deionized water) of at least about 100 g, more preferably at least about 200 g, still more preferably at least about 300 g and most preferably at least about 400 g. While pads having a total fluid capacity less than 100 g are within the scope of the invention, they are not as well suited for cleaning large areas, such as seen in a typical household, as are higher capacity pads.

In the pads there is preferably an absorbent layer which serves to retain any fluid and soil absorbed by the cleaning pad during use. While the preferred scrubbing layer, described hereinafter, has some effect on the pad's ability to absorb fluid, the preferred absorbent layer plays a major role in achieving the desired overall absorbency. Furthermore, the absorbent layer preferably comprises multiple layers which are designed to provide the cleaning pad with multiple planar surfaces.

From the essential fluid absorbency perspective, the absorbent layer is preferably capable of removing fluid and soil from any "scrubbing layer" so that the scrubbing layer will have capacity to continually remove soil from the surface. The absorbent layer also is preferably capable of retaining absorbed material under typical in-use pressures to avoid "squeeze-out" of absorbed soil, cleaning solution, etc.

The absorbent layer can comprise any material that is capable of absorbing and retaining fluid during use. To achieve desired total fluid capacities, it will be preferred to include in the absorbent layer a material having a relatively high fluid capacity (in terms of grams of fluid per gram of absorbent material). As used herein, the term "superabsorbent material" means any absorbent material having a g/g capacity for water of at least about 15 g/g, when measured under a confining pressure of 0.3 psi. Because a majority of the cleaning fluids useful with the present invention are aqueous based, it is preferred that the superabsorbent materials have a relatively high g/g capacity for water or water-based fluids.

Representative superabsorbent materials include water insoluble, water-swellable superabsorbent gelling polymers (referred to herein as "superabsorbent gelling polymers") which are well known in the literature. These materials demonstrate very high absorbent capacities for water. The superabsorbent gelling polymers useful in the present invention can have a size, shape and/or morphology varying over a wide range. These polymers can be in the form of particles that do not have a large ratio of greatest dimension to smallest dimension (e.g., granules, flakes, pulverulents, interparticle aggregates, interparticle crosslinked aggregates, and the like) or they can be in the form of fibers, sheets, films, foams, laminates, and the like. The use of superabsorbent gelling polymers in fibrous form provides the benefit of providing enhanced retention of the superabsorbent material, relative to particles, during the cleaning process. While their capacity is generally lower for aqueous-based mixtures, these materials still demonstrate significant absorbent capacity for such mixtures. The patent literature is replete with disclosures of water-swellable materials. See, for example, U.S. Pat. No. 3,699,103 (Harper et al.), issued Jun. 13, 1972; U.S. Pat. No. 3,770,731 (Harmon), issued Jun. 20, 1972; U.S. Reissue Pat. No. 32,649 (Brandt et al.), reissued Apr. 19, 1989; U.S. Pat. No. 4,834,735 (Alemany et al.), issued May 30, 1989.

Superabsorbent gelling polymers useful in the present invention include a variety of water-insoluble, but water-swellable polymers capable of absorbing large quantities of fluids. Such polymeric materials are also commonly referred to as "hydrocolloids", and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholine, and N,N-dimethylaminoethyl or N,N-diethylaminopropyl acrylates and methacrylates, and the respective quaternary salts thereof.

Well-known materials and are described in greater detail, for example, in U.S. Pat. No. 4,076,663 (Masuda et al), issued Feb. 28, 1978, and in U.S. Pat. No. 4,062,817 (Westerman), issued Dec. 13, 1977, both of which are incorporated by reference.

Preferred superabsorbent gelling polymers contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478, all of said patents being incorporated by reference.

Most preferred polymer materials for use in making the superabsorbent gelling polymers are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e. poly (sodium acrylate/acrylic acid)). Network crosslinking renders the polymer substantially water-insoluble and, in part, determines the absorptive capacity and extractable polymer content characteristics of the superabsorbent gelling polymers. Processes for network crosslinking these polymers and typical network crosslinking agents are described in greater detail in U.S. Pat. No. 4,076,663.

While the superabsorbent gelling polymers is preferably of one type (i.e., homogeneous), mixtures of polymers can also be used in the implements of the present invention. For example, mixtures of starch-acrylic acid graft copolymers and slightly network crosslinked polymers of partially neutralized polyacrylic acid can be used in the present invention.

While any of the superabsorbent gelling polymers described in the prior art can be useful in the present invention, where significant levels (e.g., more than about 50% by weight of the absorbent structure) of superabsorbent gelling polymers are to be included in an absorbent structure, and in particular where one or more regions of the absorbent layer will comprise more than about 50%, by weight of the region, the problem of gel blocking by the swollen particles can impede fluid flow and thereby adversely affect the ability of the gelling polymers to absorb to their full capacity in the desired period of time. U.S. Pat. No. 5,147,343 (Kellenberger et al.), issued Sep. 15, 1992 and U.S. Pat. No. 5,149,335 (Kellenberger et al.), issued Sep. 22, 1992, describe superabsorbent gelling polymers in terms of their Absorbency Under Load (AUL), where gelling polymers absorb fluid (0.9% saline) under a confining pressure of 0.3 psi. (The disclosure of each of these patents is incorporated herein by reference.) The methods for determining AUL are described in these patents. Polymers described therein can be particularly useful in embodiments of the present invention that contain regions of relatively high levels of superabsorbent gelling polymers. In particular, where high concentrations of superabsorbent gelling polymer are incorporated in the cleaning pad, those polymers will preferably have an AUL, measured according to the methods described in U.S. Pat. No. 5,147,343, of at least about 24 ml/g, more preferably at least about 27 ml/g after 1 hour; or an AUL, measured according to the methods described in U.S. Pat. No. 5,149,335, of at least about 15 ml/g, more preferably at least about 18 ml/g after 15 minutes. Commonly assigned U.S. application Ser. Nos. 08/219,547 (Goldman et al.), filed Mar. 29, 1994 and 08/416,396 (Goldman et al.), filed Apr. 6, 1995 (both of which are incorporated by reference herein), also address the problem of gel blocking and describe superabsorbent gelling polymers useful in overcoming this phenomena.

These applications specifically describe superabsorbent gelling polymers which avoid gel blocking at even higher confining pressures, specifically 0.7 psi. In the embodiments of the present invention where the absorbent layer will contain regions comprising high levels (e.g., more than about 50% by weight of the region) of superabsorbent gelling polymer, it can be preferred that the superabsorbent gelling polymer be as described in the aforementioned applications by Goldman et al.

Other useful superabsorbent materials include hydrophilic polymeric foams, such as those described in commonly assigned U.S. patent application Ser. No. 08/563,866 (DesMarais et al.), filed Nov. 29, 1995 and U.S. Pat. No. 5,387,207 (Dyer et al.), issued Feb. 7, 1995. These references describe polymeric, hydrophilic absorbent foams that are obtained by polymerizing a high internal phase water-in-oil emulsion (commonly referred to as HIPEs). These foams are readily tailored to provide varying physical properties (pore size, capillary suction, density, etc.) that affect fluid handling ability. As such, these materials are particularly useful, either alone or in combination with other such foams or with fibrous structures, in providing the overall capacity required by the present invention.

Where superabsorbent material is included in the absorbent layer, the absorbent layer will preferably comprise at least about 15%, by weight of the absorbent layer, more preferably at least about 20%, still more preferably at least about 25%, of the superabsorbent material.

The absorbent layer can also consist of or comprise fibrous material. Fibers useful in the present invention include those that are naturally occurring (modified or unmodified), as well as synthetically made fibers. Examples of suitable unmodified/modified naturally occurring fibers include cotton, Esparto grass, bagasse, hemp, flax, silk, wool, wood pulp, chemically modified wood pulp, jute, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, Rayon®, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The absorbent layer can comprise solely naturally occurring fibers, solely synthetic fibers, or any compatible combination of naturally occurring and synthetic fibers.

The fibers useful herein can be hydrophilic, hydrophobic or can be a combination of both hydrophilic and hydrophobic fibers. As indicated above, the particular selection of hydrophilic or hydrophobic fibers depends upon the other materials included in the absorbent (and to some degree the scrubbing) layer. That is, the nature of the fibers will be such that the cleaning pad exhibits the necessary fluid delay and overall fluid absorbency. Suitable hydrophilic fibers for use in the present invention include cellulosic fibers, modified cellulosic fibers, rayon, polyester fibers such as hydrophilic nylon (HYDROFIL®). Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemimechanical, and chemi-thermomechanical pulp processes. Recycled or secondary wood pulp fibers, as well as bleached and unbleached wood pulp fibers, can be used.

Another type of hydrophilic fiber for use in the present invention is chemically stiffened cellulosic fibers. As used herein, the term "chemically stiffened cellulosic fibers" means cellulosic fibers that have been stiffened by chemical means to increase the stiffness of the fibers under both dry and aqueous conditions. Such means can include the addition of a chemical stiffening agent that, for example, coats and/or impregnates the fibers. Such means can also include the stiffening of the fibers by altering the chemical structure, e.g., by crosslinking polymer chains.

Where fibers are used as the absorbent layer (or a constituent component thereof), the fibers can optionally be combined with a thermoplastic material. Upon melting, at least a portion of this thermoplastic material migrates to the intersections of the fibers, typically due to interfiber capillary gradients. These intersections become bond sites for the thermoplastic material. When cooled, the thermoplastic materials at these intersections solidify to form the bond sites that hold the matrix or web of fibers together in each of the respective layers. This can be beneficial in providing additional overall integrity to the cleaning pad.

Amongst its various effects, bonding at the fiber intersections increases the overall compressive modulus and strength of the resulting thermally bonded member. In the case of the chemically stiffened cellulosic fibers, the melting and migration of the thermoplastic material also has the effect of increasing the average pore size of the resultant web, while maintaining the density and basis weight of the web as originally formed. This can improve the fluid acquisition properties of the thermally bonded web upon initial exposure to fluid, due to improved fluid permeability, and upon subsequent exposure, due to the combined ability of the stiffened fibers to retain their stiffness upon wetting and the ability of the thermoplastic material to remain bonded at the fiber intersections upon wetting and upon wet compression. In net, thermally bonded webs of stiffened fibers retain their original overall volume, but with the volumetric regions previously occupied by the thermoplastic material becoming open to thus increase the average interfiber capillary pore size.

Thermoplastic materials useful in the present invention can be in any of a variety of forms including particulates, fibers, or combinations of particulates and fibers. Thermoplastic fibers are a particularly preferred form because of their ability to form numerous interfiber bond sites.

Suitable thermoplastic materials can be made from any thermoplastic polymer that can be melted at temperatures that will not extensively damage the fibers that comprise the primary web or matrix of each layer. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in the cleaning pads, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/vinyl acetate, and the like. Depending upon the desired characteristics for the resulting thermally bonded absorbent member, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber.

Suitable surfactants include nonionic surfactants such as Brij® 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/ polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., those available from Danaklon a/s, Chisso Corp., and CELBOND®, available from Hercules). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses.

Methods for preparing thermally bonded fibrous materials are described in U.S. application Ser. No. 08/479,096 (Richards et al.), filed Jul. 3, 1995 (see especially pages 16–20) and U.S. Pat. No. 5,549,589 (Homey et al.), issued Aug. 27, 1996 (see especially Columns 9 to 10). The disclosures of both of these references are incorporated by reference herein.

The absorbent layer can also comprise a HIPE-derived hydrophilic, polymeric foam that does not have the high absorbency of those described above as "superabsorbent materials". Such foams and methods for their preparation are described in U.S. Pat. No. 5,550,167 (DesMarais), issued Aug. 27, 1996; and commonly assigned U.S. patent application Ser. No. 08/370,695 (Stone et al.), filed Jan. 10, 1995 (both of which are incorporated by reference herein).

The absorbent layer of the cleaning pad can be comprised of a homogeneous material, such as a blend of cellulosic fibers (optionally thermally bonded) and swellable superabsorbent gelling polymer. Alternatively, the absorbent layer can be comprised of discrete layers of material, such as a layer of thermally bonded airlaid material and a discrete layer of a superabsorbent material. For example, a thermally bonded layer of cellulosic fibers can be located lower than (i.e., beneath) the superabsorbent material (i.e., between the superabsorbent material and the scrubbing layer). In order to achieve high absorptive capacity and retention of fluids under pressure, while at the same time providing initial delay in fluid uptake, it can be preferable to utilize such discrete layers when forming the absorbent layer. In this regard, the superabsorbent material can be located remote from the scrubbing layer by including a less absorbent layer as the lower-most aspect of the absorbent layer. For example, a layer of cellulosic fibers can be located lower (i.e., beneath) than the superabsorbent material (i.e., between the superabsorbent material and the scrubbing layer).

In a preferred embodiment, the absorbent layer comprises a thermally bonded airlaid web of cellulose fibers (Flint River, available from Weyerhaeuser, Wa) and AL Thermal C (thermoplastic available from Danaklon a/s, Varde, Denmark), and a swellable hydrogel-forming superabsorbent polymer. The superabsorbent polymer is preferably incorporated such that a discrete layer is located near the surface of the absorbent layer which is remote from the scrubbing layer. Preferably, a thin layer of, e.g., cellulose fibers (optionally thermally bonded) are positioned above the superabsorbent gelling polymer to enhance containment.

The scrubbing layer is the portion of the cleaning pad that contacts the soiled surface during cleaning. As such, materials useful as the scrubbing layer must be sufficiently durable that the layer will retain its integrity during the cleaning process. In addition, when the cleaning pad is used in combination with a solution, the scrubbing layer must be capable of absorbing liquids and soils, and relinquishing those liquids and soils to the absorbent layer. This will ensure that the scrubbing layer will continually be able to remove additional material from the surface being cleaned. Whether the implement is used with a cleaning solution (i.e., in the wet state) or without cleaning solution (i.e., in the dry state), the scrubbing layer will, in addition to removing particulate matter, facilitate other functions, such as polishing, dusting, and buffing the surface being cleaned.

The scrubbing layer can be a mono-layer, or a multi-layer structure one or more of whose layers can be slitted to facilitate the scrubbing of the soiled surface and the uptake of particulate matter. This scrubbing layer, as it passes over the soiled surface, interacts with the soil (and cleaning solution when used), loosening and emulsifying tough soils and permitting them to pass freely into the absorbent layer of the pad. The scrubbing layer preferably contains openings (e.g., slits) that provide an easy avenue for larger particulate (e.g., slits) soil to move freely in and become entrapped within the absorbent layer of the pad. Low density structures are preferred for use as the scrubbing layer, to facilitate transport of particulate matter to the pad's absorbent layer.

In order to provide desired integrity, materials particularly suitable for the scrubbing layer include synthetics such as polyolefins (e.g., polyethylene and polypropylene), polyesters, polyamides, synthetic cellulosics (e.g., Rayon®), and blends thereof. Such synthetic materials can be manufactured using known process such as carded, spunbond, meltblown, airlaid, needle punched and the like.

Cleaning pads of the present invention optionally have an attachment layer that allows the pad to be connected to an implement's handle or the support head in preferred implements. The attachment layer will be necessary in those embodiments where the absorbent layer is not suitable for attaching the pad to the support head of the handle. The attachment layer can also function as a means to prevent fluid flow through the top surface (i.e., the handle-contacting surface) of the cleaning pad, and can further provide enhanced integrity of the pad. As with the scrubbing and absorbent layers, the attachment layer can consist of a mono-layer or a multi-layer structure, so long as it meets the above requirements.

The attachment layer can comprise a surface which is capable of being mechanically attached to the handle's support head by use of known hook and loop technology. In such an embodiment, the attachment layer will comprise at least one surface which is mechanically attachable to hooks that are permanently affixed to the bottom surface of the handle's support head.

To achieve the desired fluid imperviousness and attachability, it is preferred that a laminated structure comprising, e.g., a meltblown film and fibrous, nonwoven structure be utilized. In a preferred embodiment, the attachment layer is a tri-layered material having a layer of meltblown polypropylene film located between two layers of spun-bonded polypropylene.

III. METHODS OF USE

Instructions for use are rendered in consumer-friendly language on the packaging and/or advertising (e.g., leaflets, coupons, displays, etc.). By consumer-friendly language, it is meant that consumers would be instructed how to preferably use the product, e.g., "apply five sprays of product over a two square foot area", to achieve best results. The units of measurement provided to consumers will reflect consumer understanding, e.g., English dosing units will be preferred in the United States, and metric units will be used in most other geographies. Pictures can be used, either with, or without, words in helping make the instructions consumer-friendly. Special packaging design can also be advantageously used to convey instructions in a consumer-friendly fashion. Ergonomic appeal can also make product use more intuitive, either with or without words and pictures. In particular, the packaging can be designed to facilitate proper dispensing.

Although all of the following methods described herein (below) are written in metric units; it is understood that these units will be converted into consumer-friendly language instructions in the actual product packaging, advertising etc., as illustrated above.

Floor Cleaning Using a Disposable Cleaning Pad

Optionally, and most preferably, convenience and performance can be maximized by using a system composed of a disposable cleaning pad and a mode for applying fresh solution onto the floor. The pad is composed of a laminate of non-wovens, cellulose and super-absorbent polymer. This pad is attached to a device comprising a mop head and handle. In such a system, solution application can be achieved via a separate squirt bottle or spray trigger system, or can be directly attached or built-in to the device (i.e., on the mop head or the handle). The delivery mechanism can be actuated by the operator, or can be battery-induced or electrical.

This system provides multiple benefits versus conventional cleaning modes. It reduces time to clean the floor, because the pad sucks up dirty solution. It eliminates the need to carry heavy, messy buckets. Due to the absorbent pad which absorbs and locks away dirty solution, a single pad can clean large surface areas.

Additionally, since a fresh pad is used every time, germs and dirt are trapped, removed and thrown away, promoting better hygiene and malodor control. Conventional mops, which are re-usable, can harbor dirt and germs, which can be spread throughout the household and create persistent bad odors in the mop and in the home. Through operator-controlled dosing and more efficient removal of dirty solution from the floor, better end result is also achieved.

Additionally, because the cleaning process involves use of low levels of solution in contact with the floor for much shorter periods of time relative to conventional cleaning systems, (less solution is applied on the floor and the super-absorbent polymer absorbs most of it such that volume left behind with the disposable pad and mop is only from about 1 to about 5 milliliters of solution per square meter), the system provides improved surface safety on delicate surfaces. This is particularly important for the cleaning of wood, which tends to expand and then when excess treated with excess water.

Finally, this system is well suited for pre-treating tough soil spots prior to full floor cleaning because of the controlled dosing of solution. Unlike conventional mops, this system is more effective and more convenient for removal of spills. For example, conventional mops actually wet the floor in attempting to control spills, while absorbent paper towels or cloths require the user to bend down to achieve spill removal. Finally, the implement plus pad can be designed to allow easy access to tough to clean and hard to reach areas, e.g., under appliances, tables, counters, and the like. The use of super-absorbent polymer allows a reduction in volume of the pad, i.e., the pad is thin though highly absorbent due to the super-absorbent structure being able to absorb 100 times its weight; this is achievable with conventional mops, which require greater bulk for absorption purposes (cellulose or a synthetic structures absorb only up to about from 5 to about 10 times their weight).

For best results using the disposable pad and implement cleaning system, first thoroughly sweep and/or vacuum before wet mopping. Prior to application of the solution to the areas to be cleaned, preferably apply from about 10 to about 20 milliliters in small area (e.g., about one-half a square meter) and wipe pad across area back and forth several times until solution is almost completely absorbed. This is important in that it primes the pad, allowing it to function most effectively. In an application where the dosing mechanism is separate from the implement (i.e., a detached dosing system), a priming set can optionally be to spray solution directly onto the pad, with even coverage using from about 10 to about 20 milliliters. Apply solution at rate of from about 5 to about 40 milliliters, more preferably from about 10 to about 30 milliliters per square meter, spreading the liquid out as much as possible over the area section to be cleaned. This is followed by wiping using the disposable pad.

A preferred wiping pattern consists of an up-and-down overlapping motion starting in the bottom left hand (or right hand) side of the section to be cleaned, and progressing the wiping pattern across the floor continuing to use up-and-down wiping motions. Wiping is then continued beginning at the top right (or left) side of the section to be cleaned and reversing the direction of the wipe pattern using a side-to-side motion. Another preferred wipe pattern consists of an up-and-down wiping motion, followed by an up-and-down wiping motion in the reverse direction. These thorough preferred wiping patterns allow the pad to loosen and absorb more solution, dirt and germs, and provide a better end result in doing so by minimizing residue left behind. Another benefit of the above wiping patterns is minimization of streaks as a result of improved spreading of solution and the elimination of streak lines from the edges of the pad.

The pads are versatile in that they can be used for multiple cleanings and multiple surfaces. Each pad is designed to clean one average size floor (i.e., from about 10 to about 20 square meters) with an average soil load. Pads can need to be changed sooner if floors are larger than average, or especially dirty. To determine if the pad needs changing, look at the back of the pad and ascertain if the back absorbent layer is saturated with liquid and/or dirt.

The use of the compositions herein, where no rinsing is desirable, as opposed to the types of compositions sold heretofore for treating non-bathtub/shower area surfaces including floor surfaces, walls and counter tops, provides improved performance.

IV. CONTACT ANGLE MEASUREMENT TEST METHOD

The nitrogen-containing polymers according to the present invention mitigate the negative dewetting effects of cationic antibacterial agents to provide good cleaning without unsightly streaks and haze. This is a uniquely important factor for a no-rinse floor cleaning application. Nitrogen-containing polymers are selected which can improve the surface hydrophilicity as measured by the contact angle of water on the tile surface to a value of less than 30°, preferably less than 20°, and more preferably less than 15°, as described below:

Tile Preparation: Aspen ceramic tiles (Daltile Corp., Dallas Tex.) cut to 3"×6" were cleaned prior to testing by the following procedure: Tiles were scrubbed with Dawn® neat with a plastic scrubbing pad followed by ample rinsing with tap water followed by deionized water. The tiles were subsequently wiped with reagent grade isopropanol and Kimmwipes®. Finally, the tiles were rinsed with deionized water followed by reagent grade acetone, and were allowed to air dry.

Wetting Test: The contact angle of the clean dry tiles were measured before detergent application to insure the tiles exhibit a contact angle of 10–30° for a 25 $\mu$L drop of deionized water. The contact angle is determined from the average of three drops measured on both drop sides using a level goniometer. The droplets are slowly administered to the surface using a syringe close to the surface to measure the advancing contact angle.

Two mL of the detergent solution containing the polymer as outlined below was pippeted onto the surface of the 3"×6" tile and spread with a Swiffer® WetJet™ cleaning pad (¼ the original length of the pad) with 6 back and forth strokes. The tiles are allowed to dry without rinsing for ½ hr. The contact angle for a 25 µL drop of deionized water is measured. The contact angle is determined from the average of three drops measured on both sides using a level goniometer.

The detergent solution used in this test method consists of the following:

| Components | Wt % |
| --- | --- |
| Neodol ® 11-5 | 0.03% |
| Propoxypropanol | 2.00% |
| Aminomethylpropanol | 0.01% |
| Bardac ® 2250 | 0.05% |
| Test Polymer | 0.02% |
| Dow Corning Silicone Suds Supressor | 0.00125% |
| Base to pH 9.5 | var. |
| Water and minors | q.s. |

V. EXAMPLES

The following are examples of the antimicrobial, hard surface cleaning compositions of the present invention.

(b) a cationic antimicrobial active selected from the group consisting of biguanide compounds, bis-biguanide compounds, polymeric biguanides and mixtures thereof;

(c) a nitrogen-containing polymer, wherein said nitrogen-containing polymer is selected from the group consisting of:
  (i) polyalkyleneimines and derivatives;
  (ii) modified polyamines having the formulae:

$(PA)_w(T)_x;$ (aa)

$(PA)_w(L)_z;$ (bb)

or $[(PA)_w(T)_x]_y[L]_z;$ (cc) and (iii) mixtures thereof, wherein PA is a grafted or non-grafted modified or unmodified polyamine backbone unit, T is an amide forming polycarboxylate crosslinking unit, and L is a non-amide forming crosslinking unit, provided that for compounds of type (i) and (iii) the indices w and x have values such that the ratio of w to x is from 0.8:1 to 1.5:1; for compounds of type (ii) the indices w and z have values such that said modified polyamine compounds comprises from about 0.05 to about 2 parts by weight of said L unit; for compounds of type (iii) the indices y and z have values such that said modified polyamine compound comprises from about 0.05 to about 2 parts by weight of said L unit; and (d) aqueous carrier comprising water and optional organic solvent.

| | Wt % in aqueous solution | | | | | | |
| --- | --- | --- | --- | --- | --- | --- | --- |
| Component | A | B | C | D | E | F | G |
| Surfactant | 0.005[a] | 0.01[b] | 0.05[a] | 0.03[c] | 0.09[a] | 0.04[b] | 0.07[b] |
| Polymer | 0.04[d] | 0.03[d] | 0.1[e] | 0.02[d] | 0.0[d] | 0.02[d] | 0.1[d] |
| Quaternary antibac active | 0.06[f] | 0.02[f] | 0.1[g] | 0.06[f] | 0.005[f] | 0.04[g] | 0.05[f] |
| Biguanide antibac active | 0.06[h] | 0.01[j] | 0.08[h] | — | — | 0.02[h] | 0.1[h] |
| Solvent | 00.5[k] | 2.0[k] | — | 4.0[k] | 7.0[m] | 1.0[m] | 4.0[k] |
| Buffer | — | — | — | 0.01[n] | 0.06[n] | 0.01[p] | — |
| Suds supressor | — | 0.001[r] | 0.002[r] | — | 0.003[r] | 0.001[r] | — |
| Perfume | 0.03 | 0.015 | 0.1 | 0.06 | — | 0.1 | 0.07 |
| Water | Bal. | Bal. | Bal. | Bal. | Bal. | Bal. | Bal. |

[a]Nonidet SF-3 or SF-5 (Shell Chemical)
[b]Neodol 11-5 (Shell Chemical)
[c]Alkylpolyglucoside (Henkel)
[d]Lupasol SK or Lupasol SKA (BASF)
[e]Polyethyleneimine, Molecular Weight 25,000 Daltons (BASF)
[f]Bardac 2280 (Lonza)
[g]Bardac 205M (Lonza)
[h]Chlorhexidine diacetate (Medichem, S.A.)
[j]Chlorhexidine digluconate (Medichem, S.A.)
[k]Propoxypropanol (Dow)
[m]Butoxypropanol (Dow)
[n]DMAMP (Angus)
[p]AMP-80 (Angus)
[r]Silicone suds suppressor (Dow-Corning)

What is claimed is:

1. An antimicrobial, hard surface cleaning composition comprising:
   (a) from about 0.001% to about 15%, by weight of said composition, of a surfactant selected from the group consisting of nonionic surfactant, anionic surfactant, zwitterionic surfactant, amphoteric surfactant, and mixtures thereof;

2. A cleaning composition according to claim 1, wherein said surfactant is present at a level of from about 0.001% to about 0.5%, by weight of the composition.

3. A cleaning composition according to claim 2, wherein said surfactant is present at a level of from about 0.005% to about 0.3%, by weight of the composition.

4. A cleaning composition according to claim 1, wherein said surfactant is a nonionic surfactant.

5. A cleaning composition according to claim 4, wherein said nonionic surfactant is an alkyl polyglucoside surfactant.

6. A cleaning composition according to claim 1, wherein said cationic antimicrobial active is present at a level of from about 0.005% to about 1%, by weight of the composition.

7. A cleaning composition according to claim 6, wherein said cationic antimicrobial active is present at a level of from about 0.005% to about 0.5%, by weight of the composition.

8. A cleaning composition according to claim 1, wherein said nitrogen-containing polymer is present at level of from about 0.005% to about 1%, by weight of said composition.

9. A cleaning composition according to claim 8, wherein said nitrogen-containing polymer is present at a level of from about 0.005% to about 0.3%, by weight of said composition.

10. A cleaning composition according to claim 1, wherein said nitrogen-containing polymer has a molecular weight of from about 50,000 to about 15,000,000 Daltons.

11. A cleaning composition according to claim 10, wherein said nitrogen-containing polymer has a molecular weight of from about 350,000 to about 15,000,000 Daltons.

12. A cleaning composition according to claim 1, wherein said polymeric biguanide compound is selected from the group consisting of poly(hexamethylene biguanide), poly(hexamethylene biguanide)hydrochloride, poly(hexamethylene biguanide)hydrobromide, and poly(hexamethylene biguanide)hydrogen sulfate.

13. A cleaning composition according to claim 1; wherein said bis-biguanide compound is a chlorhexidine compound.

14. A cleaning composition according to claim 1 further comprising a quaternary cationic antimicrobial active.

15. A kit for cleaning and reducing microorganisms on hard surfaces, said kit comprising:

a cleaning pad comprising an absorbent layer, wherein said cleaning pad is impregnated with the cleaning composition of claim 1.

16. The kit for cleaning and reducing microorganisms on hard surfaces of claim 15, wherein said pad further comprises an attachment layer.

17. The kit for cleaning and reducing microorganisms on hard surfaces of claim 16, wherein said pad further a scrubbing layer.

18. The kit for cleaning and reducing microorganisms on hard surfaces of claim 15, wherein said cleaning pad has a total fluid capacity less than 100 g.

19. The kit for cleaning and reducing microorganisms on hard surfaces of claim 15, wherein said cleaning pad has a total fluid capacity of at least about 100 g.

20. The kit for cleaning and reducing microorganisms on hard surfaces of claim 19, wherein said cleaning pad has a total fluid capacity of at least about 200 g.

* * * * *